United States Patent [19]

Khanna et al.

[11] Patent Number: 4,582,791

[45] Date of Patent: Apr. 15, 1986

[54] REDUCING NON-SPECIFIC BACKGROUND IN IMMUNOFLUORESCENCE TECHNIQUES

[75] Inventors: Pyare L. Khanna, San Jose; Jimmy D. Allen, Los Altos; Ian Gibbons, Menlo Park, all of Calif.

[73] Assignee: Syntex (U.S.A.) Inc., Palo Alto, Calif.

[21] Appl. No.: 539,872

[22] Filed: Oct. 7, 1983

[51] Int. Cl.$^4$ .................. G01N 53/00; G01N 33/571; G01N 33/554; G01N 33/53

[52] U.S. Cl. ........................................... 435/7; 435/5; 436/511; 436/519; 436/548; 436/800; 436/825; 252/301.16

[58] Field of Search ............... 436/501, 511, 519, 548, 436/800, 56, 825; 252/301.16; 424/7.1; 435/5, 7

[56] References Cited

U.S. PATENT DOCUMENTS

| | | | |
|---|---|---|---|
| 4,208,479 | 6/1980 | Zuk et al. | 436/537 |
| 4,261,968 | 4/1981 | Ullman et al. | 436/537 |
| 4,351,760 | 9/1982 | Khanna et al. | 424/85 |

FOREIGN PATENT DOCUMENTS

0075982  4/1983  European Pat. Off. ........ 252/301.16

OTHER PUBLICATIONS

Techniques in Immunocytochemistry, vol. 1, (1982) K. B. Pryzwansky, pp. 77–89, Academic Press, Pubs.

*Primary Examiner*—Christine M. Nucker
*Assistant Examiner*—Stephen C. Wieder
*Attorney, Agent, or Firm*—Theodore J. Leitereg; Carole F. Barrett

[57] ABSTRACT

Novel compositions and methods are provided for detecting the presence of a material of interest in a specimen on a solid surface. A composition useful for detecting the presence of a material of interest in a specimen comprises (1) a detector conjugate comprising a fluorescing moiety bonded to a compound capable of specific binding with the material of interest, or a derivative thereof, and (2) a non-detector conjugate comprising a poly(amino acid) and a compound having substantial structural and charge similarity to the fluorescing compound and no observable fluorescence, or low level fluorescence of a different wavelength than that of the fluoresing compound, in the region of fluorescence of the fluorescing compound. In the method of the invention, a specimen, on a solid surface, is combined with the detector conjugate and the non-detector conjugate, and the combination is incubated. Unbound conjugates are removed from the solid surface by washing and then the surface is irradiated with light having a wave length absorbed by the fluorescing compound. The fluorescent light emitted by the combination is observed and is a function of the amount of the material of interest present in the specimen.

21 Claims, No Drawings

REDUCING NON-SPECIFIC BACKGROUND IN IMMUNOFLUORESCENCE TECHNIQUES

BACKGROUND OF THE INVENTION

1. Field of the Invention

Immunofluorescence techniques are used for the determination of the presence of a material of interest (analyte) in a specimen (sample). Many materials of interest are present in biological specimens, for example, on a macromolecular surface such as a cell, DNA probe, etc. Specific immunofluorescence techniques involve fluorescent antibody staining. Generally, there are three techniques available: the direct method, the indirect method; and the complement staining method.

In the direct technique, a specific antiserum for an agent, which is generally the material of interest, is prepared in a laboratory animal, or a monoclonal antibody specific for the agent is prepared. The protein or more often the gamma globulin fraction of the serum, is labeled with a fluorescing compound, usually a fluorescein derivative. The antibodies against the selected agent, labeled with fluorescein, are then used to detect that agent in a specimen or tissue culture. A slide preparation of the specimen is treated with the fluorescein-labeled antiserum conjugate under suitable conditions, and, if the homologous antigen is present, an antigen-antibody reaction will take place. The specimen is then washed free of non-specifically bound conjugate. Areas of the preparation exhibiting fluorescence under the fluorescence microscope or instrument such as a solid-reading fluorometer indicate the presence of homologous antigen, provided adequate control procedures have been carried out to insure that the binding is specific.

In the indirect fluorescent antibody technique unlabeled antibody specific for a particular antigen is combined with the antigen thus giving an antigen-antibody complex. Anti-antibody (antibody for antibody) is produced according to conventional procedures and labeled witn a fluorescing compound. This conjugate combines with the antibody portion of the antigen-antibody complex produced above if the antigen is present in a sample to be analyzed. After appropriate washing, the sample is examined for the presence of fluorescence.

In the complement staining method the sample containing the material of interest is treated with unlabeled antibody specific for a particular antigen and then with a mixture of inactivated unlabeled antiserum and complement and then rinsed. This is followed by the application of, e.g., fluorescein-conjugated anti-(guinea pig complement) which binds to the site of any complement fixing antigen-antibody reaction. Fluorescent areas in the specimen indicate the sites where antigen is present.

One problem confronting users of the above-described techniques is non-specific fluorescence which tends to reduce or eliminate the effectiveness of the particular test. Generally, the specimen to be analyzed contains tissue, cells, microorganisms such as bacteria and fungi, cellular constituents, and debris. In many cases, the presence of these materials gives rise to non-specific staining (non-specific fluorescence) in fluorescent antibody techniques leading to false positive or false negative results. Those skilled in the art believed the non-specific effect to be caused primarily (1) by charge interaction between proteins in the specimen to be analyzed and proteins employed in the conjugate, (2) by other physio-chemical interactions between the proteins contributing to the non-specific staining, for example, hydrogen bonding and physical entrapment and (3) by non-specific immuno-reactions. The problem of non-specific staining is severe in virus antigen detection and the detection of bacteria or fungi.

As exemplary of the problems encountered with viruses are those problems encountered with members of the herpes virus group. Specimens to be examined for infection contain not only specific cells but also cellular debris, bacteria, and fungi. The presence of these materials gives rise to non-specific fluorescence which can mask the specific fluorescence. As a result, accuracy of the test is diminished or lost.

Various methods have been advanced for controlling non-specific staining in immunofluorescent techniques, for example, dilution of antisera; control of pH; adsorption of antisera with tissue preparations; column purification of antisera; counterstaining with a dye which contrasts with the specific dye, e.g. Evan's blue; and, with fluorescein as the fluorescent agent, using a non-specific dye such as rhodamine or a conjugate of rhodamine and a protein. Rhodamine has absorption maxima at about 515 and 552 nm and has a positive charge. None of the above methods has proven to be effective for all immunofluorescent techniques.

2. Description of the Prior Art

Applications of immunofluorescence are described by Gardner, et al., "Rapid Virus Diagnosis", Butterworth (Publishers) Inc., Boston, Massachusetts (1980) and by Goldman, "Fluorescent Antibody Methods", Academic Press, New York, N.Y. (1968). Use of a contrasting fluorescent dye (rhodamine-conjugated normal serum) as a counterstain in fixed tissue preparations is described by Smith, et al., *Proceedings of the Society of Experimental Biology and Medicine*, 102, 179–181 (1959). Rhodamine-conjugated papain as a contrasting dye in fluorescence microscopy is discussed by Alexander, et al., *Immunology* 6, 450–452 (1963). A novel dipole-dipole coupled fluorescence energy transfer acceptor, 4',5'-dimethoxy-6-carboxy-fluorescein, useful for fluorescence immunoassays is discussed by Khanna, et al., Analytical Biochemistry, 108, 156–161 (1980). In U.S. Pat. Nos. 4,318,846 and 4,351,760 there are disclosed fluorescein-poly(amino acid) conjugates as fluorescers and quenchers.

SUMMARY OF THE INVENTION

The invention described herein provides novel compositions and methods for detecting the presence of a material of interest, such as a virus, in a specimen on a solid surface. Accordingly, a composition useful for detecting the presence of a material of interest in a specimen comprises (1) a detector conjugate comprising a fluorescing moiety bonded to a compound capable of binding with an epitopic site on the material of interest, or a derivative thereof, and (2) a non-detector conjugate comprising a poly(amino acid) and a mimic compound, having substantial structural and charge similarity to the fluorescing compound and no observable fluorescence, or low level fluorescence of a different wave length than that of the fluorescing compound, in the region of fluorescence of the fluorescing compound. The non-detector conjugate is incapable of specific binding with the material of interest and capable of competitive non-specific binding with other components of the specimen in substantially the same manner as the detector conjugate.

The method of the invention is an improved immunofluorescent technique for determining the presence of a material of interest in a specimen. The specimen on a surface is combined with the detector conjugate and the non-detector conjugate and the combination is incubated. Detector conjugate that does not specifically bind to the material of interest and non-detector conjugate that does not non-specifically bind to the components of the specimen other than the material of interest are removed from the combination. The combination is then irradiated with light having a wave length absorbed by the detector conjugate and examined for fluorescence, which, if present, indicates the presence of the material of interest in the sample.

DESCRIPTION OF THE PREFERRED EMBODIMENTS

As mentioned above, the composition of the invention for detecting the presence of a material of interest in a specimen comprises a detector which may be a conjugate comprising a compound capable of specific binding with the material of interest, or a derivative thereof, and a fluorescing compound and a non-detector which may be a conjugate comprising a poly(amino acid), which is incapable of specific binding with the material of interest, and a mimic compound having substantial structural and charge similarity to the fluorescing compound and no observable fluorescence, or low level fluorescence having a wavelength different than that of the fluorescing compound, in the region of fluorescence of the fluorescing compound. By the term "specific binding" is meant that the compound is capable of recognizing and binding with one or more epitopic sites on the material of interest.

The material of interest is generally a member of a specific binding pair, usually antigen or antibody. The present invention is applicable generally in any technique in which fluorescence is employed in conjunction with an antigen-antibody reaction, such as, e.g., in the detection of the presence of infectious agents such as a virus, bacteria, fungi, chlamydia, cancer antigen, surface antigens, and the like; in serology tests; etc.

Representative of viruses leading to infections which can be detected by the present method, by way of illustration and not limitation, are myxoviruses, e.g., rubella virus, canine distemper virus, rinderpest virus, respiratory syncytial virus, influenza (A, B, and C) viruses, para influenza viruses, mumps virus, and measles virus; picornaviruses; poliovirus, for example, coxsackievirus, echoviruses, and rhinoviruses; rabies variola; adenoviruses; herpes virus hominis (herpes I and II) miscellaneous viruses in the herpes virus group, for example, herpes simplex, virus B, herpes varicella-herpes zoster, and cytomegalovirus; Epstein-Barr virus; pox viruses, e.g., variola (smallpox), vaccinia, poxvirus bovis, and paravaccinia; arboviruses including eastern equine encephalitis virus, western equine encephalitis virus, sindbis virus, chikugunya virus, semliki forest virus, malfora virus, St. Louis encephalitis virus, California encephalitis virus, Colorado tick fever virus, yellow fever virus, and dengue virus; reoviruses (types 1-3); hepatitis A and hepatitis B virus; tumor viruses; Rauscher leukemia virus; gross virus; Maloney leukemia virus; and the like. The invention is particularly of importance in the detection of infection by herpes virus hominis because other methods do not provide the requisite reduction in background interference.

Representative of bacteria leading to infections which can be detected by the present method, by way of illustration and not limitation, are: Corynebacteria including *Corynebacterium diptheriae;* Streptococci including *Streptococcus pyogenes, Streptococcus pneumoniae; Streptococcus salivarius;* Staphylococci including *Staphylococcus aureus, Staphylococcus albus;* Neisseriae including *Neisseria meningitidis, Neisseria gonorrhoeae;* Pasteurellae including *Pasteurella pestis, Pasteurella tularensis;* Brucellae including *Brucella melitensis, Brucella abortus, Brucella suis;* Aerobic Spore-forming Bacilli including *Bacillus anthracis, Bacillus subtilis, Bacillus megaterium, Bacillus cereus;* anaerobic spore-forming bacilli including *Clostridium botulinum, Clostridium tetani, Clostridium perfringens, Clostridium novyi, Clostridium septicum, Clostridium histolyticum, Clostridium tertium, Clostridium bifermentans, Clostridium sporogenes;* Mycobacteria including *Mycobacterium tuberculosis hominis, Mycobacterium bovis, Mycobacterium avium, Mycobacterium leprae, Mycobacterium paratuberculosis;* Actinomycetes (fungus-like bacteria) including *Actinomyces israelii, Actinomyces bovis, Actinomyces naeslundii, Nocardia asteroides, Nocardia brasiliensis;* the Spirochetes including *Treponema pallidum, Treponema pertenue, Treponema carateum, Borrelia recurrents, Leptospira icterohaemorrhagiae, Leptospira canicola, Spirillum minus, Streptobacillus, moniliformis;* Mycoplasmas including *Mycoplasma pneumoniae;* other pathogens including *Listeria monocytogenes, Erysipelothrix rhusiopathiae, Streptobacillus moniliformis, Donvania granulomatis, Bartonella bacilliformis;* Rickettsiae (bacteria-like parasites) including *Rickettsia prowazekii, Rickettsia mooseri, Rickettsia rickettsii, Rickettsia conorii, Rickettsia australis, Rickettsia sibericus, Rickettsia akari, Rickettsia tsutsugamushi, Rickettsia burnetii, Rickettsia quintana.*

Representation of fungi leading to infections which may be detected employing the present method, by way of illustration and not limitation are *Cryptococcus neoformans; Blastomyces dermatidis; Histoplasma capsulatum; Coccidioides immitis; Paracoccidioides brasiliensis; Candida albicans; Aspergillus fumigatus; Mucor corymbifer (Absidia corymbifera);* Phyconycetes including *Rhizopus oryzae, Rhizopus arrhizus, Rhizopus nigricans; Sporotrichum schenkii; Fonsecaea pedrosoi; Fonsecaea compacta; Fonsecaea dermatidis; Cladosporium carrionii; Phialophora verrucosa; Aspergillus nidulans; Madurella mycetomi; Madurella grisea; Allescheria boydii; Phialosphora jeanselmei; Microsporum gypseum; Trichophyton mentagrophytes; Keratinomyces ajelloi; Microsporum canis; Trichophyton rubrum;* and *Microsporum andouini.*

Also included within the material of interest that may be detected according to the present method are antigens on the surface of cells, e.g., blood group antigens such as, A-B-O haptens, M-N-haptens, Rh-Hr haptens, and haptens of other specificities which may be found on the surface of red blood cells.

The specimen is generally of biological origin, usually taken from a site where the presence of the material of interest is suspected. Generally, the components of the specimen are macromolecular in nature, usually comprising whole cells. The procedures for taking and preparing a specimen for examination by immunofluorescence are well known in the art. Specimens containing the material of interest may also contain other substances such as cellular debris, bacteria, fungi, mucus and pus. The specimen may be derived from tissue such as blood, mucus, or other body fluid, as well as from an organ. The specimen may be, for example, urethral, cervical, pharyngeal, rectal, etc.

The detector conjugate is the conjugate which recognizes a material of interest or a derivative of the material of interest. The detector conjugate comprises a compound capable of specific binding with a material of interest or a derivative thereof. By "derivative of the material of interest" is meant a substance having the material of interest bound thereto, which substance is recognizable in a fluorescent antibody technique, for example, an antigen-antibody complex as generated in an indirect fluorescent antibody technique or a complex of antigen-antibody-complement in a complement staining fluorescent antibody technique.

Generally, as mentioned above, the material of interest is a member of a specific binding pair. Thus, the compound capable of binding with the material of interest will be the other member of the specific binding pair. "Specific binding pair" means two different molecules where one of the molecules has an area on the surface or in a cavity which specifically binds to a particular spatial and polar organization of the other molecule. The members of the specific binding pair are referred to as ligand and receptor (anti-ligand). Usually, the members of the specific binding pair are antigen and antibody. Illustrative receptors include antibodies, enzymes, natural receptors and the like. Particularly preferred as part of the detector conjugate are antibodies produced primarily by introducing an immunogenic substance into the blood stream of a living animal or those antibodies produced by biotechnology, particularly monoclonal antibody techniques. The polyclonal or monoclonal antibodies thus produced would be specific for the material of interest in the specimen.

Also included as part of the detector conjugate is a fluorescing portion. Generally, the fluorescing moiety is a fluorescing compound which absorbs light at wavelengths of above about 450 nanometers and emits light at wavelengths in excess of 500 nanometers. The preferred fluorescing compound is fluorescein or a fluorescein derivative and such materials have been reported in the literature. The parent molecule is fluorescein or 3',6'-dihydroxyspiro-[(isobenzofuran-1-3H),9'-(9H)xanthen]-3-one.

Fluorescein is most frequently used for fluorescent antibody investigations. Generally, the florescein is in the form of an isothiocyanate (FITC) for coupling to a protein. Fluorescein derivatives having the appropriate absorption and emission characteristics are available and have been used. For example (using the numbering system based on the parent molecule) some of the derivatives known are:

2',7'-di(n-hexyl) or di(n-heptyl)-4',5'-dibromo-4,7-dichloro- are reported in C.A. 31, 1621;
2',7'-di(n-hexyl)-, C.A. 31, 1621;
2',7'-di(alkyl)-, C.A. 31, 1388;
2',7'-diethyl or 2',7'-dibutyl-, C.A. 27, 5056;
2',7'-dimethyl-, C.A. 83, 18972S;
2',4',5',7'-tetrabromo-5 or 6-carboxy-, C.A. 63, 13210H.

Other fluorescing compounds which may be used in the present invention include 2,7-dialiphatic-6-hydroxy-3H-xanthene-3-ones as disclosed in U.S. Pat. No. 4,351,760 particularly described at column 1, lines 61–68 and column 2, lines 1–32 (the disclosure of which is incorporated herein by reference in its entirety). Another set of fluorescein derivatives which may find use in the present invention are taught in U.S. Pat. No. 4,318,846 at column 2, lines 41–68 to column 3, lines 1–34 (the disclosure of which is incorporated herein by reference). These compounds are normally 2,7-di(aliphatic ether)substituted-9-phenyl-6-hydroxy-3H-xanthene-3-ones which are unsubstituted at the 4',5'-positions or are substituted at the 4',5'-positions with other than oxy substituents.

Rhodamine and rhodamine derivatives may also be employed in the present invention as the fluorescing compound in the detector conjugate.

As mentioned above, the composition for detecting the presence of a material of interest in a specimen also comprises a non-detector conjugate which means a conjugate not capable of specific binding with the material of interest or a derivative thereof or with the detector conjugate. The non-detector conjugate comprises a poly(amino acid) and a mimic compound. Generally, the ratio of mimic compound to protein in the non-detector conjugate for use in the detection of herpes virus will be about 10:1 to 30:1, preferably about 20:1 to 25:1. The optimum ratio of mimic compound to protein for each particular organism can be determined on a case by case basis using the teaching disclosed herein.

The poly(amino acid), including antibodies, enzymes, and antigens, generally has a molecular weight of from about 2,000 to $1 \times 10^7$, usually from about 5,000 to $1 \times 10^6$. Generally, the poly(amino acid) is a globulin, particularly an immunoglobulin, more particularly IgG or IgM. The poly(amino acid) preferably is structurally similar to the compound capable of binding with the material of interest or derivative thereof which forms part of the detector conjugate. The poly(amino acid) in the non-detector conjugate generally should be capable of interacting with the specimen by means of charge-charge interaction, hydrogen bonding, and physical entrapment in the same manner as the protein portion of the detector conjugate. The poly(amino acid) should not be capable of binding with either the material of interest in the specimen or with the detector conjugate or its components. Usually, when the compound capable of binding with the material of interest or a derivative thereof, which forms part of the detector conjugate, is an antibody, the poly(amino acid) of the non-detector conjugate will be immunoglobulin, e.g., IgG or IgM which is not capable of binding with either the material of interest or with the detector conjugate.

The non-detector conjugate further comprises a compound having substantial structural and charge similarity to the fluorescing compound, thereby being a "mimic" of the fluorescing compound. The mimic compound has no observable fluorescence, or a low level of fluorescence having a wavelength (color) different from that of the fluorescing compound, in the region of fluorescence of the fluorescing compound.

By the term "substantial structural and charge similarity" is meant that the structure and charge of the mimic compound is sufficiently similar to that of the fluorescing compound such that the mimic compound, as part of the non-detector conjugate, interacts by means of hydrogen bonding, charge-charge interaction, and physical entrapment with components of the specimen other than the material of interest in substantially the same manner as the fluorescing compound of the detector conjugate interacts by means of hydrogen bonding, charge-charge interaction, and physical entrapment with those components of the specimen.

For example, when the fluorescing moiety is fluorescein bound to antibody in the detector conjugate, the mimic compound, bound to IgG in the non-detector conjugate will be structurally similar to fluorescein and be negatively charged. For example, the mimic compound may be a 4',5'-di(aliphatic ether) substituted-9-phenyl-6-hydroxy-3H-xanthene-3-one, differing from fluorescein by the presence of alkoxy groups, usually methoxy groups, at the 4',5'-positions. Such compounds may differ further by the presence or absence of a phenyl group at the 9-position.

The presence of an oxy group, such as an alkoxy group of about 1-8, usually 1 to 6, preferably 1-3 carbon atoms in the 4',5'-position affords sufficient retention of structural and charge similarity to fluorescein so that the latter may be used in a non-detector conjugate of the invention. In that capacity, such non-detector conjugate functions efficiently to give a substantial reduction in background fluorescence in an immunofluorescent antibody test for herpes virus. It has been found that the combined detector conjugate and non-detector conjugate wherein the mimic compound differs from fluorescein by the presence of methoxy groups at the 4',5'-positions are effective in immunofluorescent antibody tests for herpes virus.

The particular mimic compound employed in the non-detector conjugate is thus dependent on the fluorescing compound employed in the detector conjugate. When the fluorescing compound is a flourescein derivative which is substituted at the 2',7'-positions with oxy substituents, usually symmetrically, in accordance with the teaching of U.S. Pat. No. 4,318,846, a mimic compound which may be used in accordance with the present invention is one which is described in the above-identified patent, particularly at column 2, lines 41-68, column 3, and column 4, lines 1-22 and has substantial structural and charge similarity to the fluorescing compound. The mimic compounds described in the aforementioned patent are fluorescein derivatives which are oxy substituted, i.e., substituted with an alkoxy group of about 1 to 8, usually 1 to 6, preferably 1 to 3, carbon atoms, at the 4',5'- positions and which may be unsubstituted at the 1',8'- and 2',7'-positions or substituted thereat with other than oxy substituents. These compounds exhibit substantially no fluorescence and are negatively charged, having substantial structural similarity to the fluorescing compound. The preferred detector conjugates may be appropriately selected, using the teaching embodied herein, from compounds disclosed in the aforementioned patent.

When the fluorescing compound is rhodamine, a mimic compound as part of the non-detector conjugate in accordance with the present invention will have substantial structural similarity to rhodamine and be positively charged.

Preferred compositions for detecting the presence of a material of interest in a specimen comprise a detector conjugate which includes a monoclonal antibody covalently linked with a fluorescein derivative. Preferred non-detector conjugates forming part of the present composition comprise immunoglobulin covalently linked to a mimic compound which is a fluorescein derivative substituted in the 4',5'-position by alkoxy, preferably methoxy.

The non-detector conjugate should have a structural, spatial, polar, and electronic character similar to that for the detector conjugate. In this way, maximum reduction in non-specific background in fluorescent antibody tests may be achieved.

The amount of detector conjugate in the composition of the invention should be sufficient to result in an acceptable level of fluorescence in a positive test. The amount of non-detector conjugate in the present composition should be sufficient to substantially reduce non-specific background fluorescence. In the case of detection of herpes virus the detector conjugate and the non-detector conjugate will generally be present in the composition of the invention in the proportion of approximately 1 to 4 parts (by weight) of non-detector conjugate per part of detector conjugate. Generally, the composition of the invention is prepared in an aqueous medium which is usually buffered. The concentration of the detector conjugate and the non-detector conjugate in the medium is dependent on the specific test to be performed and the amount of specimen used. Generally, for standard antibody fluorescent techniques for herpes virus, the concentration of the detector conjugate in the medium will be about 10 to 75 μg/ml, preferably about 25 to 50 μg/ml. The concentration of the non-detector conjugate is related to the concentration of the detector conjugate, the type of specimen, the number of cells, the presence of cell debris, bacteria, and fungi, etc. Generally, the concentration of non-detector conjugate employed for standard antibody fluorescent techniques for herpes virus is about 25–200 μg/ml, preferably about 50–100 μg/ml. For example, for herpes virus I and II the concentration of the non-detector conjugate will be 50–100 μg/ml. The above ratios and concentration ranges are merely exemplary for herpes virus and are not meant to be a limitation. The particular concentrations employed in a specific test for an organism may be deterined by pilot trials using the above as guidelines. The concentration of the non-detector conjugate should not be so great as to significantly reduce the signal from the detector conjugate.

The pH of the composition is usually about 5 to 11, preferably about 6 to 9, more preferably, 7 to 8. As mentioned above, buffer may be present in the aqueous medium. For this purpose, one may use such buffers as phosphate, tris, carbonate, borate, and the like.

In a method for determining the presence of a material of interest in a specimen in accordance with the present invention, the specimen is combined with the detector conjugate and the non-detector conjugate, usually contained in an aqueous medium. Normally, the specimen is bound to a surface, such as a glass slide, for example, by securing a specimen from the source of infection on a swab and applying the specimen to the surface. The composition containing the detector and non-detector conjugates is next applied to the slide, the amount of composition applied generally being dependent on the size of the slide and the amount of specimen contained thereon. The slides which are employed in the present technique may or may not contain indentations or small wells on their surface formed by the interfacing of a plastic layer, having a plurality of holes, with the glass slide surface. For those slides having indentations one may use, for example, about 2 to 50 μl, preferably about 20–30 μl of the present aqueous composition per well on the surface of the slide. Generally, for slides with about 10 wells (about 6 mm diameter) approximately 25 μl of the composition would be employed per well and for slides with about 3 to 4 wells (about 8–10 mm diameter), about 30 μl of the present composition per well would be used. Again, the above amounts are merely illustrative for the detection of herpes virus and the optimum amounts for other organisms can be determined by one skilled in the art following the teaching herein. For slides with no indentations, one may simply flood the entire slide with the composition of the invention.

After the specimen and the composition containing the detector and non-detector conjugates have been combined, the combination on the surface is incubated at a temperature and for a time to allow for binding to occur between components of the specimen and the above conjugates. Usually the combination is incubated for a period of about from 5 to 60 minutes, preferably about 15 to 45 minutes at a temperature of about 15° to 40° C., preferably ambient temperature to 37° C. It is usually desirable to carry out the incubation in a moist atmosphere, such as in a moist chamber.

After incubation the solid surface with the combination is treated under mild conditions to remove unbound conjugate therefrom. To this end the slide can be contacted or washed with water, usually distilled or deionized water, or an aqueous buffered medium of pH about 6 to 9 for a period of time to remove unbound conjugates. Generally, the combination is contacted with the water for a period of about 10 seconds to 3 minutes. Customarily, the combination is contacted with the water by dipping the combination in water for the above period of time. Consequently, when the specimen is applied to a slide which is subsequently treated with the conjugate composition described above, the slide after incubation is generally immersed in water for the appropriate period of time to remove unbound conjugate. Generally, it is desirable to remove residual liquid from the slide after the above washing. Accordingly, the slide may be blotted or pressed against a water absorbing material. It should be obvious that other means for removing water from the slide will be suggested to those skilled in the art. It may be desirable to allow the specimen sample to dry.

It is also desirable to add a small amount of a mounting fluid and then cover the slide with a cover slip (second slide) to improve the optics in the test as is customary in the art.

Next, the combination on the surface is irradiated with light having a wave length absorbed by the fluorescing compound which forms part of the detector conjugate. The amount and morphology (shape) of fluorescent light emitted by the combination is observed. The fluorescent light detected is a function of the presence and amount of material of interest present in the specimen. When a slide is used, the slide, prepared as above, is examined under a fluorescence microscope.

The above-described approach is particularly applicable to the direct method involved in fluorescent antibody staining techniques. The invention described herein is applicable also to the indirect fluorescent antibody technique. However, in this approach, the detector conjugate would comprise a fluorescing compound and a compound capable of binding with a derivative of the material of interest. For example, the material of interest may be a virus antigen. In the indirect technique the virus antigen is first combined with unlabeled specific antibody against the virus antigen. The detector conjugate would therefor comprise a fluorescing compound and antibody for the antibody which is now bound to the virus antigen.

The invention may also be employed in the complement staining method wnere, of course, the detector conjugate would comprise a flourescing compound and a compound capable of binding with an antigen-antibody-complement complex.

One advantage of the present invention is that non-specific background fluorescence which arises in fluorescent techniques of this type, such as a fluorescent antibody technique, is substantially reduced. Consequently, the accuracy achieved by employing the method and compositions of the present invention is substantially enhanced over that obtained with the known techniques for removing non-specific background fluorescence in these analyses.

Another advantage of the present invention is that the non-detector conjugate generally has little or no observable fluorescence. In the event that the non-detector conjugate has some low level of observable fluorescence, such fluorescence is of a different wave length, i.e., color, than that of the fluorescing compound and is easily differentiated. This is important because the fluorescent signal generated by the detector conjugate is readily observable and is not interfered with; as a result an accurate signal is given.

The success of the present invention is surprising because closely related compounds do not provide the requisite removal of non-specific background fluorescence to avoid false positive tests. For example, the components of the non-detector conjugate, e.g., poly(amino acid) and mimic compound, if employed individually, separately or in combination, in a composition for detecting the presence of a material of interest in a specimen, do not adequately reduce non-specific background fluorescence so that an accurate test may be achieved. Furthermore, conjugates of rhodamine isothiocyanate and a protein such as IgG or albumin are not as effective as the present materials in a fluorescent antibody technique employing fluorescein or a fluorescein derivative because (1) rhodamine is a positively charged molecule whereas fluorescein is negatively charged, (2) rhodamine is also fluorescent and therefore interferes in detection, and (3) a ratio of rhodamine to protein greater than about 10:1 is difficult to obtain for a rhodamine-protein conjugate in an aqueous environment.

We have found that the mimic compound of the non-detector conjugate in accordance with the present invention should have little or no fluorescence in the region of fluorescence of the fluorescing compound, and, together with the protein portion of the non-detector conjugate, should be capable of non-specific interaction, i.e., structural and charge interaction, with components of the specimen other than the material of interest in substantially the same manner as the detector conjugate. Thus, it is important that the mimic compound have the same charge and hydrophobic properties as the fluorescing compound. In this way non-specific interaction between the specimen and the detector conjugate is considerably reduced and accuracy of the test is enhanced even where standard laboratory equipment is used.

EXAMPLES

The invention is demonstrated further by the following illustrative examples.

All temperatures not otherwise indicated are centigrade. Percents and parts not otherwise indicated are by weight, except for mixtures of liquids which are by volume. Abbreviations which are employed are as follows: NHS-N-hydroxysuccinimide; h-hour; PBS-phosphate buffered saline; IgG-immunoglobulin G; DMSO-dimethylsulfoxide; FITC-fluorescein isothiocyanate; UV-ultraviolet.

A. Preparation of conjugate of 4',5'-dimethoxy-5-carboxy-3',6'-dihydroxyspiro[isobenzofuran-1(3H),9'-(9H)xanthen]-3-one ("4',5'-dimethoxy-5-carboxyfluorescein") and rabbit IgG (non-detector conjugate). Preparation of 4',5'-dimethoxy-5-carboxy-fluorescein and its NHS ester were carried out according to the teaching of Khanna et al., supra. Rabbit IgG (5 mg) in 0.1M sodium carbonate (pH 9.2) was mixed with 2 mg of the above NHS ester and the mixture was stirred for one hour at room temperature. Next, the mixture was applied to a Sephadex G-25 column using 0.05 M phosphate buffer, pH 8. Based on UV absorption at 518 nm and 280 nm, the ratio of mimic compound to protein was estimated to be about 20-30 molecules of mimic compound per molecule of protein.

B. Preparation of conjugate of fluorescein and monoclonal antibodies to herpes virus I and II (detector conjugate).

Monoclonal antibodies to herpes virus I and II were prepared according to conventional techniques.

The procedure for the conjugation of fluorescein to the above monoclonal antibodies was similar to that employed in Section A of this Example. Accordingly, monoclonal antibody preparation for herpes virus I from above in 0.1 M sodium carbonate (pH 9.2) was mixed with FITC in DMSO (10 mg/ml). Generally, the ratio of FITC to monoclonal antibody was 50 μg per mg. The mixture was stirred for one hour at room temperature and then applied to a Sephadex G-25 column using 0.01 M carbonate buffer, pH 9.2. Based on UV absorption at 496 nm and 280 nm, the ratio of fluorescein/protein was estimated to be about 5 molecules of fluorescein per molecule of protein.

In a similar manner, monoclonal antibody preparation for herpes virus II was conjugated with FITC.

C. Slide test.

The non-detector conjugate of A and the detector conjugate of B were combined in an aqueous medium at pH 7.2. The detector conjugate was present at a concentration of 25 μg/ml. The concentration of the non-detector conjugate was varied as follows: 300 μg/ml, 100 μg/ml, 30 μg/ml, 10 μg/ml and also 0 μg/ml (control).

A specimen was obtained which consisted of a cervical or lesion scraping of cells uninfected or infected with herpes virus. The specimen was applied to the surface of standard glass slides containing four wells. Each slide was contacted with 30 μl of either composition 1, 2, 3 or 4 or the control. After contact, each slide was incubated at ambient temperature (20°-25°) for a period of 30 minutes. Then, each slide was washed with distilled water to remove residual composition and blotted to remove water.

The resulting specimens on the slides were placed under a fluorescent microscope (excitation at 470-490 nm, emission at 520 nm). The samples were observed for fluorescent staining. Each slide was visually examined under the fluorescent microscope and subjectively rated as to the extent of fluorescent antibody staining indicative of a positive test and the intensity of the background staining. The results are summarized in the following Table 1. The intensity of fluorescence was estimated as follows: (a) for the values in Table 1 representing specific specimen staining: 4+:maximal fluorescence, brilliant yellow-green, clear cut cell outline; sharply defined non-staining of cell; 3+:less brilliant yellow-green fluorescence, clear cut cell outline, sharply defined non-staining center of cell; 2+: less brilliant, but definite fluorescence, less clear-cut cell outline, non-staining center area fuzzy; 1+: very subdued cell-wall fluorescence, cell center is indistinguishable from cell wall; (b) for the values in Table 1 representing background staining: in addition to the above; minus(—): background staining absent; ±: indiscriminate background staining of low intensity.

TABLE 1

| Organism | | Extent of flourescent staining | | | | |
| --- | --- | --- | --- | --- | --- | --- |
| | | Non-detector conjugate (μg/ml) | | | | |
| | | 300 | 100 | 30 | 10 | 0(control) |
| Herpes Virus I | Specific | 3+ | 3.5+ | 4+ | 4+ | 4+ |
| | Background | — | — | — | ± | ± |
| Herpes Virus II | Specific | 1+ | 1+ | 2+ | 2+ | 2+ |
| | Background | — | — | — | 1+ | 2+ |

The above data indicate that the combination of detector and non-detector conjugates at appropriate concentrations in accordance with the present invention is effective in reducing or eliminating background fluorescence in fluorescent antibody techniques.

What is claimed is:

1. A composition for detecting the presence of a material of interest in a specimen, which comprises:
   a detector conjugate comprising a fluorescing compound and a compound capable of binding within an epitopic site on the material of interest or a derivative thereof and
   a non-detector conjugate comprising a poly(amino acid) and a minic compound having substantial structural and charge similarity to the fluorescing compound, and no observable fluorescence in the region of fluorescence of the fluorescing compound, or low level fluorescence relative to the fluorescing compound at a wavelength different from that of the fluorescing compound in the region of fluorescence of the fluorescing compound, said non-detector conjugate being incapable of specific binding to the material of interest or a derivative thereof.

2. The composition of claim 1 in an an aqueous medium.

3. The composition of claim 1 wherein the material of interest is antigenic.

4. The composition of claim 1 wherein the material of interest is selected from the group consisting of viruses, bacteria, fungi, chlamydia, surface antigens, and cancer antigens.

5. The composition of claim 1 wherein the fluorescing compound is florescein.

6. The composition of claim 1 wherein the compound capable of binding with the material of interest or a derivative thereof is antibody specific for the material of interest or a derivative thereof.

7. The composition of claim 1 wherein the poly(amino acid) is a globulin.

8. The composition of claim 1 wherein the poly(amino acid) is a blood plasma protein.

9. The composition of claim 1 wherein the poly(amino acid) is an immunoglobulin.

10. The composition of claim 1 wherein the poly(amino acid) is an enzyme.

11. The composition of claim 1 wherein the fluorescing compound is fluorescein and the mimic compound is a fluorescein derivative substituted at the 4',5'-positions with oxy substituents.

12. The composition of claim 11 wherein the oxy substituents are alkoxy of from 1 to 8 carbon atoms.

13. The composition of claim 1 wherein the fluorescing compound is fluorescein and the mimic compound is 4′,5′-dimethoxy-5-carboxy-3′,6′-dihydroxyspiro[isobenzofuran-1(3H),9′-(9H)xanthen]-3-one.

14. The composition of claim 1 wherein the fluorescing compound is a fluorescein derivative substituted at the 2′,7′-positions with oxy substituents and the mimic compound is a fluorescein derivative substituted at the 4′,5′-positions with oxy substitutents.

15. The composition of claim 1 wherein the material of interest is a herpes virus antigen.

16. The composition of claim 1 wherein the compound capable of binding with the material of interest is antibody to herpes virus.

17. The composition of claim 1 wherein the compound capable of binding with the material of interest is a monoclonal antibody to herpes virus.

18. The composition of claim 1 in an aqueous buffered medium containing about 1 to 4 parts by weight of non-detector conjugate per part by weight of detector conjugate.

19. The composition of claim 1 wherein the ratio of mimic compound to poly(amino acid) is about 10:1 to 30:1.

20. A method for determining the presence of a material of interest in a specimen, which comprises:
  (a) combining the specimen and the composition of claim 1;
  (b) incubating the combination;
  (c) removing unbound conjugate from the combination;
  (d) irradiating the combination with light having a wavelength absorbed by the fluorescing compound; and
  (e) observing the amount of the fluorescent light emitted, and the morphology of, by the combination, wherein the fluorescent light emitted is related to the presence of the material of interest in the sample.

21. The metnod of claim 20 wherein the material of interest is selected from the group consisting of viruses, bacteria, fungi, chlamydia, surface antigens, and cancer antigens.

* * * * *

UNITED STATES PATENT AND TRADEMARK OFFICE
CERTIFICATE OF CORRECTION

PATENT NO. : 4,582,791
DATED : April 15, 1986
INVENTOR(S) : Pyare L. Khanna, Jimmy D. Allen and Ian Gibbons It is certified that error appears in the above—identified patent and that said Letters Patent is hereby corrected as shown below:

Column 12, Line 27, change the word "within" to --with--.

Column 14, line 19, change "metnod" to --method--.

Signed and Sealed this

Thirtieth Day of September 1986

[SEAL]

Attest:

Attesting Officer

DONALD J. QUIGG

Commissioner of Patents and Trademarks